United States Patent [19]

Berger, Jr. et al.

[11] Patent Number: 4,806,488

[45] Date of Patent: Feb. 21, 1989

[54] LIGAND-RECEPTOR ASSAYS EMPLOYING SQUARATE DYE COMPOSITIONS

[75] Inventors: Donald E. Berger, Jr., San Jose; Thomas L. Tarnowski, So. San Francisco; Edwin F. Ullman, Atherton, all of Calif.

[73] Assignee: Syntex (U.S.A.) Inc., Palo Alto, Calif.

[21] Appl. No.: 773,401

[22] Filed: Sep. 6, 1985

[51] Int. Cl.$^4$ .......................................... G01N 33/536
[52] U.S. Cl. .................................. 436/536; 436/501; 436/543; 436/546; 436/547; 436/800; 436/815; 435/810; 424/7.1; 424/85.8; 424/88; 514/690; 530/403; 530/387
[58] Field of Search ............... 436/536, 543, 546, 547, 436/800, 501, 815; 424/7.1, 85, 88; 530/403; 435/810; 514/690

[56] References Cited

U.S. PATENT DOCUMENTS 4,166,105  8/1979  Hirschfield ........................ 436/800

FOREIGN PATENT DOCUMENTS 0176252  4/1986  European Pat. Off. .

OTHER PUBLICATIONS

Chemical Abstracts, vol. 102, (1985), No. 70326j.
Angew, Chem. International. Edit., vol. 5, No. 10, 1966, p. 894, Dr. H. E. Sprenger et al., "Condensation Products of Squaric Acid and Tertiary Aromatic Amines".

Primary Examiner—Robert J. Warden
Assistant Examiner—Stephen C. Wieder
Attorney, Agent, or Firm—Theodore J. Leitereg

[57] ABSTRACT

Novel assays for ligands and receptors employing novel compounds that are conjugates of squarates dyes and members of a specific binding pair (sbp) are disclosed. The sbp members are selected from the group consisting of ligand and its complementary receptor. The sbp member is covalently or non-covalently bound to the squarate dye, which usually has an absorption maximum greater than 600 nanometers. The novel conjugates are employed in assays for determining the presence or amount of an sbp member analyte in a sample suspected of containing such analyte. Kits comprising such novel conjugates are also disclosed.

82 Claims, No Drawings

4,806,488

LIGAND-RECEPTOR ASSAYS EMPLOYING SQUARATE DYE COMPOSITIONS

BACKGROUND OF THE INVENTION

1. Field of the Invention

Fluorescent compounds find wide application because of their ability to emit light upon excitation with energy within certain energy ranges. By virtue of this ability, fluorescers have found employment as labels in chemical or biological processes, e.g. assays. That is, various compounds can be conjugated to a fluorescent compound, the conjugate subjected to some type of partitioning, and the fate of the conjugate determined by irradiating the sample with light and detecting the zone in which the conjugate exists.

This technique can be employed in immunoassays, involving specific binding pairs, such as ligands and receptors, e.g., antigens and antibodies. By conjugating a fluorescer to one of the members of the specific binding pair and employing various protocols, one can provide for partitioning of the fluorescer conjugate between a solid phase and a liquid phase in relation to the amount of antigen in an unknown sample. By measuring the fluorescence of either of the phases, one can then relate the level of fluorescence observed to a concentration of the antigen in the sample.

Alternatively, one can avoid partitioning of the fluorescent label by providing for a mechanism which varies the fluorescence of the label, depending upon the label environment in a liquid medium. For example, in addition to labeling one of the members of the specific binding pair with the fluorescer, one may label the other member with a quencher, that is, a molecule which is able to absorb the excitation energy of the fluorescer molecule, preventing the emission of a photon. The quenching then will occur only when the two members of the specific binding pair are associated and the fluorescer and quencher thereby achieve the required spatial proximity for quenching.

2. Description of the Prior Art

U.S. Pat. No. 3,998,943 discloses an immunoassay involving a ligand-fluorescer conjugate employing steric inhibition of simultaneous binding of antibody for ligand and antibody for fluorescer, where the antibody for fluorescer substantially quenches the fluorescence. U.S. Pat. No. 3,996,345 describes an immunoassay involving fluorescer-quencher pairs, which employs a conjugate of a fluorescer bonded to one member of a specific binding pair and a conjugate of a quencher bonded to the same or different member of a specific binding pair. The assay is dependent upon the degree to which the quencher and fluorescer are brought within quenching proximity based on the amount of analyte in the medium. Novel conjugates of fluorescers and quenchers with poly(amino) acids are disclosed in U.S. Pat. Nos. 4,351,760 and 4,318,846. A dye tagged reagent is described in U.S. Pat. No. 4,166,105. Digoxigenin immunogens, antibodies, labeled conjugates and related derivates are discussed in U.S. Pat. No. 4,469,797.

Various squarate dyes are discussed by Sprenger, et al., *Angew. Chem.*, 80, 541 (1968) [*Angew. Chem. internatl Edit*, Vol. 7: 530–535 1968]; Sprenger, et al., *Angew. Chem.*, 79; 581, 1967; Sprenger, et al., *Angew. Chem. internat. Edit.*, 5: 894, 1966; and Maahs, et al., ibid., 5: 888, 1966.

The use of laser beams and slits to differentiate particles based on their relative size by the correlation of fluorescence fluctuations in a relatively large sample volume is described by Briggs et al., *Science*, 212: 1266–1267, 1981, and by Nicoli et al., *Proc. Natl. Acad. Sci.*, USA, 77: 4904–4908, 1980.

SUMMARY OF THE INVENTION

The present invention concerns novel compounds that are conjugates of squarate dyes, usually having an absorption maximum greater than 600 nanometers, and members of a specific binding pair. The specific binding pair members are selected from the group consisting of ligand and its complementary receptor. The novel compounds are employed in assays for determining the presence or amount of an analyte in a sample containing the analyte. Novel assay methods employing the above conjugates or water compatible squarate dyes are also included in the invention. Kits comprising the novel compounds are also provided.

DESCRIPTION OF THE SPECIFIC EMBODIMENTS

The present invention provides an improvement in compounds used in an assay for determining an analyte in a sample where the compounds are conjugates of a dye and a specific binding pair member. The improvement comprises employing a squarate dye as the dye in the conjugate. The present invention also includes novel assay methods employing the squarate dye conjugates or water compatible squarate dyes in conjunction with a helium/neon laser.

Before proceeding further with the description of the specific embodiments of the present invention, a number of terms will be defined.

Analyte—the compound or composition to be measured, the material of interest, which is usually a member of a specific binding pair and may be a ligand, which is mono- or polyvalent, usually antigenic or haptenic, and is a single compound or plurality of compounds which share at least one common epitopic or determinant site.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, gestogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, quanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6,000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand-any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Support or surface—a porous or non-porous water insoluble material. The surface can be hydrophilic or capable of being rendered hydrophilic and can be formed from inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Binding of sbp members to the surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245: 3059 (1970) or Cautrecases, *J. Biol. Chem.*, 245, 3059 (1970).

Particles—particles of at least about 50 nm and not more than about 50 microns, usually at least about 100 nm and less than about 25 microns, preferably from about 0.2 to 5 microns diameter. The particle may be organic or inorganic, swellable or non-swellable, porous or non-porous, preferably of a density approximating water, generally from about 0.7 to about 1.5 g/ml, and composed of material that can be transparent, partially transparent, or opaque.

The organic particles will normally be polymers, either addition or condensation polymers, which are readily dispersible in the assay medium. The organic polymers will also be adsorptive or functionalizable so as to bind, either directly or indirectly, an sbp member.

The particles can be derived from naturally occuring materials, naturally occurring materials which are synthetically modified and synthetic materials. Among organic polymers of particular interest are polysaccharides, particularly cross-linked polysaccharides, such a agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like. Inorganic polymers include silicones, glasses, available as Bioglas, and the like. Natural or synthetic assemblies such as liposomes, phospholipid vesicles, and cells can also be employed.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to a support or a compound of the invention through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.*, 245 3059 (1970). The length of a linking group to a compound of the invention may vary widely, depending upon the nature of the compound being linked, the effect of the distance between the compound being linked and the particle on the binding of sbp members and the analyte and the like.

Squarate dye—a dye having the structural element of cyclobutenonolate, generally being a condensation product of squaric acid (dihydroxycyclobutenedione) and an active compound such as a pyrrole or a aniline. The squarate dye generally has an absorption maximum greater than 600 nanometers, and preferably is 620 to 650 nm.

The molar extinction coefficient for the squarate dye at the wavelength of the exciting light should be as high as practical and should be greater than 10,000, preferably greater than 100,000 square centimeters per mole. The squarate dyes should have a high quantum yield, normally greater than 0.05, preferably greater than 0.3.

Label—A member of the signal producing system that is conjugated to an sbp member. The label can be any squarate dye as defined herein.

Signal Producing System—The signal producing system may have one or more components, at least one component being a squarate dye or precursor of a squarate dye. The signal producing system includes all of the reagents required to produce a measurable signal including means for causing electronic excitation of the squarate dye. A preferred means can be, for example, a He/Ne laser with an emission wavelength at 633 nm. However, other light sources having an excitation wavelength greater than 600 namometers can be employed. Other components of the signal producing system can include enzymes, chemiluminescent compounds, quenchers, substrates, etc.

Quencher—those compounds having absorption maxima at or greater than 600 nanometers. Such compounds preferably have little or no observable fluorescence and efficiently quench the fluorescence of a squarate dye-sbp member conjugate in accordance with the present invention. Examplary of such compounds are Gallocyanine, Celestine Blue, Delphine Blue, Methylene Green, and the like.

Group or functionality imparting water solubility—a functionality incorporated into a compound of the invention which imparts water solubility to the compound, that is, renders the compound soluble in water to an extent of at least one nanomolar. Such functional group or functionality can include a sulfonate, phosphate, phosphonate, carboxylate, hydroxyl, amine, ether, amide, and the like. The group imparting water solubility generally comprises from 1 to 30 atoms, preferably 1 to 12 atoms, other than hydrogen, which atoms are selected from the group consisting of carbon, oxygen, nitrogen, sulfur, phosphorus, and halogen of atomic number 9 to 53. Such group can be part of the squarate dye prior to the formation of the conjugate of the squarate dye and the sbp member. Consequently, the squarate dyes can be conjugated to a wide variety of sbp members including poly(amino)acids without significantly altering the water solubility of the sbp member or without having the spectroscopic properties of the squarate dye adversely affected.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

The compounds of the invention are novel fluorescent compounds comprising a squarate dye conjugated to an sbp member. The squarate dye has an absorption maximum greater than 600 nanometers.

For the most part the compounds of the invention will have the following formula

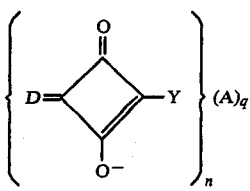

wherein:
D and Y are the same or different and each comprises a chain of from 1 to 6 moieties selected from the group consisting of —CH= and —N=, said chain having alternating single and double bonds and terminating in a functionality selected from the group consisting of O, S, and nitrogen, wherein the sum of the number of said moieties and said terminal functionality in both D and Y is an even number, preferably within the range of from 6 to 10, said chain, or part thereof including the terminal functionality, being aliphatic or part of one or more alicyclic or aromatic rings, or a combination thereof, said chain or rings, or functionalities having zero, one, or more substituents comprising from 1 to 30 atoms, usually 1 to 12 atoms, more usually 1 to 4 atoms, other than hydrogen, which atoms are selected from the group consisting of carbon, oxygen, nitrogen, sulfur, halogen of atomic numbers 9 to 53, arsenic, silicon, selenium and phosphorus, wherein said substituents may be taken together to form one or more rings which may be alicyclic or aromatic, wherein at least one of D or Y is bonded to A;

A is a group comprising at least one member of a specific binding pair (sbp) consisting of ligand and its complementary receptor; the sbp member can be bound to a polymeric backbone; preferred sbp members are antigens, antibodies and haptens;

When the sbp member is not bound to a polymer, n is a number on the average of from about 1 to 20, usually 2 to 15, preferably 4 to 10; and, when the sbp member is bound to a polymer, n is a number on the average from about 2 to $10^4$, usually 10 to $10^3$, preferably 20 to 100. Reference to "on the average" means that some sbp member molecules may have more or less than n number of dye molecules, but the mixture of conjugate molecules will have on the average, n number of dye molecules per conjugate; and q is 1 or 2.

The squarate dye and the sbp member can be bound together either covalently or non-covalently. Covalent binding can result from a bond or a linking group. A wide variety of linking groups may be employed to bond the squarate dye and the sbp member. The choice of linking group will vary widely, depending upon the available functionalities or functionalities which may be present or readily introduced into the dye or sbp member, the desired length of the linking arm, the desirability of having the linking arm provide for a particular environment, chemical property or physical property, e.g. positively or negatively charged, solubility enhancement, dipole effects, or the like. The linking group preferably includes a non-oxo-carbonyl, carbamoyl, thiocarbamoyl, sulfonyl, amino, thio, particularly a functionality having a non-oxo-carbonyl, and sulfur analogs thereof.

For the purposes of this disclosure non-oxo-carbonyl shall include the carbonyl group or carboxylic acids

the nitrogen containing iminocarbonyl group of amidic acids

and the sulfur containing thionocarbonyl group of thio acids

The term noncovalent means that the bond is formed by other than the sharing of electrons. Such bonds are formed primarily by electrostatic interactions, for example, hydrogen bonding, dipole dipole interactions, or van der Walls interactions.

Compounds included within the scope of the invention have the formula

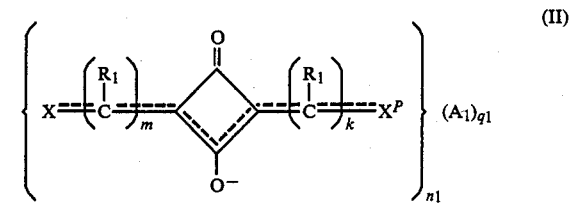

wherein:
m is 1 to 4; preferably 3 to 4;
k is 1 to 4; preferably 3 to 4;
m+k is an even number;
X is O, S, or N(R$_1$)$_2$;
p is (—) when X is O or S and (+) when X is N(R$_1$)$_2$;
R$_1$ is hydrogen and when not hydrogen is independently selected from a group of substituents having from 1 to 30 atoms other than hydrogen, usually 1 to 12 atoms, more usually 1 to 4 atoms, selected from the group consisting of carbon, oxygen, nitrogen, sulfur, halogen of atomic number 9 to 53, arsenic, silicon, selenium, and phosphorus, wherein R$_1$ may be taken together with one or more other R$_1$s to form one or more rings, usually five or six membered rings, and wherein a hydrogen atom on at least one R$_1$ is replaced by a bond or a linking group to A$_1$; for example, when m and k are each 4, R$_1$ on carbon 1 R$_1$ on carbon 4 can be taken together to form an ethylene group as part of a benzene ring, or, when m and k are each 2, X is N(R$_1$)$_2$ and one R$_1$ of N(R$_1$)$_2$ can be taken together with R$_1$ on the carbon bearing N(R$_1$)$_2$ to form a five member ring; additionally, a benzene ring can be fused to the five membered ring;
n$_1$ is n;
A$_1$ is A; and
q$_1$ is q.

Compounds of the following formula are within the scope of the invention:

$$\left\{ D_1 = \begin{array}{c} O \\ \square \\ O^- \end{array} = Y_1 \right\}_{n_2} (A_2)_{q_2} \quad (\text{III})$$

wherein:
$A_2$ is A;
$n_2$ is n;
$q_2$ is $q_1$;
$D_1$ is independently selected from the group consisting of

[structures showing $(R_2)_2^+N=$ phenyl group with $(R_2)_4$, benzazole with Z, $(R_2)_s$, $(R_2)_4$, $R_2$; and $(R_2)_2N-$ phenyl-CH= with $(R_2)_4$, and benzazole-CH= variant]

$Y_1$ is independently selected from the group consisting of

[structures showing $\}-$phenyl$-N(R_2)_2$ with benzazole variant, HC= with Z, $(R_2)_s$, $(R_2)_4$, $R_2$]

$HC=$phenyl$=^+N(R_2)_2$, and benzazole cation variant

Z in $D_1$ and Z in $Y_1$ are independently selected from the group consisting of carbon, nitrogen, oxygen, sulfur, and selenium;
$R_2$ is $R_1$; and
s is 2 when Z is carbon, 1 when Z is nitrogen, and 0 when Z is oxygen, sulfur, or selenium.

For example, $D_1$ can be

[structure of $(R_2)_2\overset{+}{N}=$ phenyl $=\}$ with $(R_2)_4$]

wherein $R_2$ bound to nitrogen is independently selected from the group consisting of methyl and a group imparting water solubility and $R_2$ bound to carbon is hydrogen, wherein a hydrogen atom or at least one $R_2$ is replaced by a bond or a linking group to $A_2$.

In another example, $D_1$ can be

[benzazole structure with $(R_2)_4$, Z, $(R_2)_s$, CH, $R_2$]

wherein $Z(R_2)_s$ is isopropylidene.

Preferred compounds are selected from the group consisting of $$\left\{ (R_4)_t\text{—indolinium—}CH=\square(O,O^-)=CH\text{—indoline—}(R_4)_t \right\}_{n_3} (LA_3)_{q_3} \quad (IV)$$

with $R_3, R_3$ groups, $R_3$ on N;

and $$\left\{ \begin{array}{c} R_3 \\ R_3 \end{array} N^+ = \text{phenyl} = \square(O,O^-) = \text{phenyl} - N \begin{array}{c} R^3 \\ R_3 \end{array} \right\}_{n_3} (LA_3)_{q_3} \quad (V)$$

with $(R_4)_t$ groups wherein:
$A_3$ is a member of a specific binding pair, preferably antigen, hapten, or antibody;
$n_3$ a number on the average from about 1 up to the molecular weight of $A_3$ divided by 5000, usually 2 to 15, preferably 4 to 10;

t is 1 or 2;

$q_3$ is q;

$R_3$ is independently selected from the group of substituents having 1–10, preferably 1 to 6, carbon atoms, 0–6, preferably 1 to 2, oxygen atoms, and 0–3 preferably 0 to 1, nitrogen atoms, and may be taken together to form an alicylic or aromatic ring; exemplary of such substituents are carboxymethyl, aminoethyl, dihydroxy, propyl, ethyl, methyl and like;

$R_4$ is independently selected from the group consisting of hydroxyl, hydrogen, phosphate, phosphonate, sulfonate, nitro, halogen, amino, and $R_3$; and L replaces any hydrogen or $R_3$ and is a bond or a linking group to $A_3$.

Preferred compounds are those compounds wherein at least one $R_3$ on nitrogen has a hydrogen replaced by L, particularly where every remaining $R_3$ on nitrogen is lower alkyl of from 1 to 5 carbons, or wherein t is 1 and $R_4$ is hydroxyl, or wherein L is selected from the group consisting of non-oxo-carbonyl, carbamoyl, thiocarbamoyl, thio and amino.

Generally, the squarate dye should contain a group or functionality imparting water solubility. However, water insoluble squarate dyes can be employed provided that a medium for conducting the conjugation of the squarate dye to the sbp member contains a substance that will render the squarate dye soluble. Such substance can be, for example, a detergent or a complexing agent such as cyclodextrin. Water insoluble squarate dyes can also be used when the sbp member does not require an aqueous medium for conjugation to the dye. Furthermore, when the squarate dye and the sbp member are non-covalently bound together, water solubility is not necessary and it may additionally be desirable to incorporate into the squarate dye substituents that impart hydrophobicity, such as, e.g., a hydrocarbon group having from 4 to 30 carbon atoms, preferably 6 to 20 carbon atoms, or substituents that provide for enhanced affinity of the dye for a receptor. For example, biotin can be attached to a squarate dye to provide for coupling to a ligand attached to avidin.

A particular example of a compound of the invention has the formula condensation can be carried out under reflux in an alkanol/benzene solvent mixture. The resulting product can be collected and purified by, for example, recrystallization, distillation, chromatography, or the like. The group or functionality imparting water solubility to the compound of the invention can be part of an initial reactant for the condensation or it can be introduced after the condensation by conventional techniques.

The squarate dyes can be conjugated to sbp members by techniques that are known in the art. Such conjugation can be the result of direct bond formation between the squarate dye and the sbp member. On the other hand, a linking group as described above can be introduced into the squarate dye or the sbp member for attachment to the other component. A functionality for attachment such as carboxylic acid, hydroxyl, thio, amino, aldehydic, amido, activated ethylenes such as maleimide, sulfonic acids, and the like can be introduced into the squarate dye or the sbp member if such functionality is not originally present in the dye or the sbp member. Methods of conjugation involving sbp members are described in, e.g., U.S. Pat. No. 3,817,837, the disclosure of which is incorporated herein by reference.

The compounds of the invention have properties that are very desirable for their use in assays. The compounds have a high extinction coefficient, a high quantum efficiency, approaching one, chemical stability, and satisfactory Stokes shift. Furthermore, where the compounds are to be used in the presence of serum or other composition, which is in itself fluorescent, the compounds absorb energy in a substantially different range from that absorbed by the other compounds in the medium. As mentioned above, the present compounds have an absorption maximum greater than 600 nanometers.

One aspect of the present invention involves an assay for a material of interest in a sample suspected of containing the material of interest. In the assay a fluorescent compound is employed to generate a signal in relation to the presence or amount of the material of interest in said sample and an energy source for excitation of said fluorescent compound is also employed. The improve-

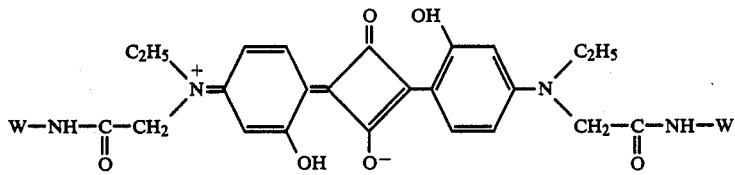

(VI)

wherein: W is selected from the group consisting of antibody for digoxin and a digoxin analog capable of binding to such antibody. For example, the digoxin analog can be 3-deoxy-3-digoxigenin.

The compounds of the present invention can be prepared by a reaction sequence, the individual steps of which are separately known in the art. Some of the squarate dyes of the present invention can be made according to the procedures described by Sprenger et al., *Angew. Chem.*, 80, 541 (1968); Springer et al., *Angew. Chem.*, 79, 581 (1967); Sprenger et al., *Angew. Chem., internat. Edit.*, 5, 894 (1966); and Maaks et al., *Angew. Chem. internat. Edit.*, 5, 888 (1966). In general, squaric acid (dihydroxycyclobutenedione) is condensed with an active compound such as a pyrrole or an aniline. The condensation is conducted under conditions for removing water from the reaction mixture. For example, the ment in such assay comprises employing a squarate dye, particularly a water compatible squarate dye having an absorption maximum greater than 600 nanometers, as the fluorescent compound and a helium/neon laser as the energy source. The squarate dyes can be rendered water compatible by incorporating a group or functionality imparting water solubility into the squarate dye. Alternatively, the squarate dye can be rendered water compatible by employing about 0.01 to 10%, of a detergent such as Triton X-100 or sodium dodecyl sulfate, $1 \times 10^{-4}$ to $1 \times 10^{-2}$M cyclodextrin or the like, in the assay medium. In another alternative, 0.02–20 μm latex particles or particles such as liposomes, cells and the like can be stained with the squarate dye to provide water compatibility.

Another aspect of the present invention involves an improvement in an assay for an analyte in a sample suspected of containing said analyte where the analyte is an sbp member. The method involves an sbp member conjugated to a dye and the improvement of the present invention comprises employing as the dye a squarate dye.

For example a fluorescent assay can employ as a reagent a fluorescent compound conjugated to a member of a specific binding pair. Such assay is for the determination of an analyte which is also a member of a specific binding pair. The binding of the conjugate to the analyte or a specific binding pair member complex of the analyte is indicative of the presence of the analyte. The present improvement comprises employing in the fluorescent assay a reagent that is a squarate dye conjugated to a member of a specific binding pair. Another example is a method for detecting the presence of a determinant site or a receptor by employing a fluorescent reagent having a fluorescent compound bound to a member of a specific binding pair. The binding of the fluorescent reagent to the determinant site or the receptor, or a specific binding pair member complex of the determinant site or the receptor, is determined as indicative of the presence of the determinant site or the receptor. The improvement of this invention comprises employing a fluorescent reagent that is a conjugate of a squarate dye and a member of a specific binding pair. The method has particular application where the determinant site or receptor is associated with a cell such as, e.g., being present on the cell surface.

The present conjugates can be used for determining qualitatively, semiquantitively or quantitatively an analyte in a sample. Where compounds are to be detected in physiological fluids, the sample may include serum, urine, saliva, lymph or the like. Where the compound of interest is involved in chemical processing or ecological concerns, the sample may be an aqueous medium, or may be obtained by extraction from an organic medium, soil, inorganic mixtures, or the like.

Another reagent in the assay can be a compound of the invention wherein the sbp member is a receptor for the analyte.

As indicated previously, the compounds of this invention can include squarate dyes conjugated to compounds which may be measured by known immunoassay techniques. The conjugates are reagents which compete in an assay medium for the analyte in a sample. Therefore, the conjugate retains a sufficient proportion of the structure of the analyte to be able to compete with the analyte for a receptor for analyte.

The assays may involve a change of spectroscopic properties due to a change in environment about the spectroscopically active compound or the bringing together of a fluorescer-quencher pair within sufficient proximity for the quencher to interact with the fluorescer. Alternatively, methods can be employed which involve the separation of associated and unassociated fluorescer and the detection of the fluorescer in one or both of the fractions.

In carrying out the method an aqueous medium will normally be employed. Other polar solvents may also be employed, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 5.4–9.5. The pH is chosen so as to maintain a significant level of binding between sbp members while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method and usually constant temperatures during the period of the method. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique, and the concentration of the analyte will normally determine the concentration of the other reagents.

While the concentrations of the various reagents will generally be determined by the concentration range of interest of the analyte, the final concentration of each of the reagents will normally be determined empirically to optimize the sensitivity of the assay over the range of interest. The total binding sites of the members of the specific binding pair which are complementary to the analyte will be not less than about 0.1 times the minimum concentration of interest based on binding sites of the analyte and not more than about 10,000 times the maximum concentration of interest based on analyte binding sites, usually about 0.1–1000 times, more usually about 0.3–10 times the maximum concentration of interest. For ligand analyte, where labelled ligand is employed, the concentration range of the labelled ligand based on equivalents will generally be not less than about $10^{-6}$, more usually not less than $10^{-2}$, times the minimum concentration of interest and not greater than 100, usually not greater than 10, times the maximum concentration of interest.

The concentration of the compound of the invention in the assay medium is dependent on the type of assay, heterogeneous or homogeneous, competitive or direct, etc. Normally, the compound of the invention will be present in the assay medium in a concentration about $10^{-6}$ to $10^{-15}$, usually about $10^{8}$ to $10^{13}$M.

The order of addition of the various reagents may also vary and is dependent on much of the same considerations mentioned above.

The present assay method has application both to hetereogeneous and homogeneous assays. Exemplary heterogeneous assays are found in U.S. Pat. Nos. 4,256,834 and 4,261,968. Homogeneous immunoassays are exemplified by immunofluorescence methods such as those disclosed in U.S. Pat. No. 3,993,345, enzyme channeling techniques such as those disclosed in U.S. Pat. No. 4,233,402, and other enzyme immunoassays as discussed in Maggio, supra, and in U.S. Pat. No. 3,817,837. The assay can be competitive or direct and can involve compounds of the invention that are either labeled ligand or labeled receptor.

In one approach in accordance with the invention for detecting the presence or amount of analyte in a sample suspected of containing said analyte wherein said analyte is an sbp member consisting of ligand and its complementary receptor. The method comprises (1) combining in an assay medium the sample, as described above, a conjugate of a squarate dye and an sbp member, and a second sbp member, wherein the two sbp members are complementary to the analyte and (2) determining the effect of said sample on the fluorescence of compound I as related to the presence or amount of analyte in said sample.

The second sbp member can be conjugated to a compound capable of quenching the fluorescence of the conjugate when both spb members are bound to the analyte. Alternatively, the second sbp member can be bound to a particle or to a surface or support to permit separation of conjugate that binds to the support from the conjugate remaining in solution.

For example, in one technique, a quencher for the squarate dye is employed. One reagent is a compound of the invention comprising a conjugate of a squarate dye and an analog of a ligand analyte. Another reagent is a conjugate of quencher and an sbp member that is a receptor for analyte. The ligand analyte in the sample and the ligand analyte analog in the reagent compete with receptor for analyte. When the receptor for analyte binds to the labeled ligand analyte analog, the fluorescer and quencher are brought within quenching distance. A similar assay employing fluorescent compounds not within the scope of this invention is extensively described in U.S. Pat. No. 3,996,345. The assay technique is described beginning with column 17 and ending at column 23, which description is incorporated herein by reference. The ratios of fluorescent compound to ligand and receptor is described in the above-cited patent at columns 4-6, which description is incorporated herein by reference.

In a related but different approach one reagent can be a compound of the invention that is a conjugate of a squarate dye and a receptor for the ligand analyte. Another reagent is a conjugate of a quencher for the squarate dye and a receptor for the ligand analyte. When the two reagents above are combined with the sample and brought together by the prescence of ligand analyte, the squarate dye and the quencher are brought within quenching distance. A typical quencher can be, e.g., gallocyanine, which can be conjugated through an amide bond to an sbp member.

The assay is carried out by combining the squarate dye conjugate and the quencher conjugate in conjunction with the sample. The fluorescence is determined in comparison to an assay medium having a known amount of analyte.

In another example the compound of the invention is a conjugate of a squarate dye and a receptor for the ligand analyte. Ligand or ligand analog is bound to a support or to a particle. Similar assays are described in U.S. patent application Ser. No. 964,099, now U.S. Pat. No. 4,275,149, filed Nov. 24, 1978. These assays are predicated upon having the fluorescer molecule available in bulk solution for interaction with a signal modulator or bound to a particle, where the particle environment prevents the interaction. Alternatively, the particle can provide an environment which modulates the fluorescent signals when the fluorescer conjugate is bound to the particle.

Another approach involves steric exclusion in that receptors for the ligand and for the squarate dye are employed, where simultaneous binding of the receptor for the ligand and receptor for the dye is inhibited. Furthermore, when the receptor for the dye is bound to the dye, the fluorescence of the dye is substantially diminished. Further reduction, if not complete inhibition of fluorescence, can be achieved by conjugation of quencher to receptor for the dye. A similar assay is extensively described in U.S. Pat. No. 3,998,943, issued Dec. 21, 1976. The assay is described in columns 3-5 of the subject patent, which description is incorporated herein by reference.

Generally, the method involves combining in an assay medium the sample suspected of containing the analyte, the conjugate of the sbp member and the dye, and other reagents in accordance with a particular assay protocol chosen. The sample is then exposed to a source of excitation. The fluorescence is determined either as a rate or equilibrium mode, readings being taken within about 1 second to 1 hour after all materials have been combined for a rate mode, while for an equilibrium mode, readings may be taken for as long as up to about 24 hours or longer.

As a matter of convenience, the reagents employed in the present invention can be provided in a kit in packaged combination with predetermined amounts of reagents for use in assaying for an analyte in a sample. The reagents will include a compound of the invention as disclosed above, and, where appropriate, conjugates of quenchers and sbp members or other reaction partners for the compound of the invention required to provide the detectable signal. In addition, other additives such as ancillary reagents may be included. The relative amounts of the various reagents may be varied widely, to provide for concentractions in solution of the reagents which substantially optimize the sensitivity of the assay. The reagents can be provided as dry powders, usually lyophilized, including excipients, which on dissolution will provide for a reagent solution having the appropriate concentrations for performing the assay.

EXAMPLES

The invention is demonstrated further by the following illustrative examples. All temperatures are in degrees Centigrade (°C.). Parts and percentages herein are by weight unless otherwise specified.

The following abbreviations were used:
DMF—dimethylformamide
BGG—bovine gamma globulin
PBS—phosphate buffered saline (0.01M sodium phosphate, 0.15M NaCl, 0.005M $NaN_3$, pH7.0)
tlc—thin layer chromatography
NHS—N-hydroxy succinimide
EDAC—ethyl-3-(dimethylaminopropyl)carbodimide hydrochloride
PBS/BCD—PBS containing 0.01M β-cyclodextrin.
PBS/10%BGG—PBS containing 100 mg BGG/ml
BGG—bovine gamma globulin
PBS/BGG—PBS containing 10 mg/ml of BGG
PBS/BGG/Triton—PBS/BGG containing 10 mg/ml of Triton X-100
PBS/SDS—PBS containing 50 mg/ml of SDS
SDS—Sodium dodecyl sulfate

EXAMPLE 1

Preparation of Aminodextran

Into a 50-ml round bottomed flask fitted with a thermometer insert was placed 5.0 g of Dextran T500 (Pharmacia), 15 ml of deionized $H_2O$, and a magnetic stir bar.

The mixture was stirred and heated to 80° (oil bath). To this was added 1.875 g of solid Zn(BF$_4$)$_2$·xH$_2$O (Alfa). When solution was complete and the temperature had stabilized at 80°, 10.03 g of epichlorhydrin was added dropwise over 5-15 min. The mixture was stirred and heated at 80° for 3 hr. Heating was then stopped, and the reaction mixture was allowed to stir and cool to room temperature overnight.

The clear solution was added dropwise with vigorous stirring to 250 ml of methanol. The white precipitate that formed was washed with methanol and dried under N$_2$. Further drying overnight in a vacuum dessicator gave 4.71 g of chlorodextran. Elemental analysis of lyophilized material purified on a Sephadex G-25 column packed and eluted with H$_2$O showed 3.385 mmol Cl/mg chlorodextran.

A solution of 1 g of chlorodextran in 1 ml of deionized water was added dropwise with stirring to 40 ml of concentrated aqueous NH$_3$. The reaction mixture was stirred 3 days. After concentration (rotovap) to 5 ml the solution was added dropwise to 500 ml of vigorously stirred methanol. The resulting white precipitate was collected by filtration, washed under N$_2$ with methanol, and dried under N$_2$. Additional drying in a vacuum dessicator overnight gave 1.13 g of aminodextran as a white powder. Elemental analysis (C, H, N, Cl) corresponded to $2.30 \times 10^{-4}$ mmol amine/mg aminodextran as the hydrochloride salt. Elemental analysis of a lyophilized sample that had been purified on Sephadex G-25 eluted with aqueous 1M NH$_3$ showed $2.98 \times 10^{-4}$ mmol amine/mg aminodextran. The crude material was used without further purification.

EXAMPLE 2

Preparation of Digoxigenin-Linked Aminodextran

Digoxin containing a general tritium label (500 μl of a 1 mCi/ml solution in 1:9 toluene:ethanol, 20 Ci/mmol) and unlabeled digoxin (2.0 g, 2.56 mmol) were dissolved in 50 ml of ethanol. To this was added 75 ml of ethanol, 100 ml of distilled H$_2$O, and 1 ml of concentrated aqueous HCl. The solution was refluxed for 45 minutes.

The solution was then cooled, neutralized with aqueous 5N NaOH, and evaporated to 100 ml. The resulting white precipitate was collected by filtration, recrystallized from 80% aqueous ethanol, and dried under vacuum to give 557 mg of tritium labeled digoxigenin: mp 205°-207°; 0.169 mCi/mmol, $3.7 \times 10^8$ cpm/mmol.

The tritium-labeled digoxigenin was oxidized to the 3-ketodigoxigenin with Pt and O$_2$ by the procedure of Tamm and Gubler (*Helv. Chim. deta,* 42, 239, (1959)).

The tritium labeled 3-ketodigoxigenin was converted into the tritium-labelled carboxymethoxime by the following method:

A clear solution of 3-ketodigoxigenin (228 mg, 0.59 mmoles), carboxymethoxyamine hemihydrochloride (140 mg, 0.64 mmole, Aldrich Chemical Company), and sodium acetate (294 mg, 3.6 mmole) in methanol (18 ml, dried over molecular sieves 3 A) was allowed to stir at room temperature under nitrogen for 3 hours. The tlc of an aliquot of sample showed the complete formation of oxime derivative (Rf 0.33; 0.5:1:10/HOAc-MeOH-CHCl$_3$, Silica gel plate). The resulting reaction product was stripped to dryness, the residue dissolved in 32 ml 5% NaHCO$_3$ at 5°-10° C., and was extracted with 3×20 ml chloroform. The chloroform extracts were discarded. The bicarbonate layer was acidified at 5°-10° C. with 28 ml of 1N hydrochloric acid to pH 2-3 and was extracted with 10×25 ml ethyl acetate. The ethyl acetate extracts were washed with saturated sodium chloride and dried over anhydrous sodium sulfate. Evaporation of solvent gave the tritium labeled 3-ketodigoxigenin carboxymethoxime as a solid which recrystallized from a mixture of methanol-ethyl acetate-hexane: mp. 202°-220° (dec); IR (Kbr): 3600 cm$^{-1}$-3200 cm$^{-1}$ (acid).

The NHS ester of H-digoxigenin carboxymethyloxime was prepared in situ by addition of 1.18 mg of EDAC to a stirred solution at 0° to 2.76 mg of $^3$H-digoxigenin carboxymethyloxime prepared as above with and 0.849 mg of NHS in 30 μl of freshly distilled (CaH$_2$) DMF, followed by a second addition of 0.2 mg of EDAC after 1 hr.

To 10 mg of aminodextran prepared in Example 1 in 1.0 ml of 0.1M sodium pyrophosphate (pH8.5) at 0° was added over 2-3 min by microliter syringe 9.5 μl of the above solution of $^3$H-digoxigenin NHS ester in DMF. After two hr the reaction mixture was washed free of small molecules on an Amicon filtration device by dilution of the reaction mixture to 15 ml with 14 ml of 0.1M sodium pyrophosphate containing 10 mg/ml sodium cholate (pH 8.5 ) and concentrating to 1.5 ml followed by 10 mM sodium phosphate buffer (pH7.0) as the dilution/concentration buffer. The final solution was diluted with the sodium phosphate buffer to 7.0 ml. Analysis for aminodextran by optical rotation gave 1.377 mg aminodextran/ml solution. Scintillation counting as analysis for digoxigenin gave $4.702 \times 10^{-5}$ mmol digoxigenin/ml solution. Aminodextran and 3H-digoxigenin carboxymethyloxime were used as standards. A value of $3.415 \times 10^{-5}$ mmol digoxigenin/mg aminodextran was thus determined.

EXAMPLE 3

Preparation of Digoxigenin-Linked Magnetic Particles

Magnetic particles prepared by polymerization of acrylic acid and acrolein derivatives in the presence of Rembaum magnetic iron oxide as described by Rembaum et al. in *J. Immunol. Methods* (1982) 52: 341-351 were used as the magnetic particle. To 5.0 mg of this material, reported to contain surface aldehyde groups, in a 1.5-ml polypropylene centrifuge tube was added 182 μl of the solution of digoxigenin-linked aminodextran (dig-dextran) prepared as described in Example 2. The tube was capped and vertically rotated overnight. After a 2-min centrifugation to collect the particles, scintillation counting of the supernatant showed that 36.6 μmol of digoxigenin per mg of magnetic particles had adhered to the particles. The particles were washed with brief sonication with five 200 μl portions of PBS followed by centrifugation and decentation of the washes. Scintillation counting of the washes showed about 45% of the counts to remain with the particles. This gave a final analysis of $6.90 \times 10^{-7}$ mmol digoxigenin/mg particles and $1.73 \times 10^{-6}$ mmol digoxigenin/ml suspension.

EXAMPLE 4

Preparation of Squarate Dye-Linked Antidigoxin

1-[4-(diethylamino)-2-hydroxyphenyl]-3-[4-(N-ethylcarboxymethylamino)-2-hydroxyphenyl]-2,4-dihydroxycyclobutenediylium dihydroxide, bis(inner salt) (DECAS) was prepared by refluxing with azeotropic water removal equimolar amounts of 3-diethylamino phenol, squaric acid, and N-ethyl-N-3-hydroxyphenyl glycine methyl ester prepared as in Example 6 in 2:1 (v/v) n-butanol:benzene followed by isolation of the monomethylester-dye by silical gel chromatography. The deep blue methyl ester was hydrolyzed with NaOH to give DECAS after acidification.

The NHS ester of DECAS was generated by addition of 1.3 mg of EDAC to a solution of 3.0 mg of DECAS and 0.99 mg of NHS in 120 μl of freshly distilled ($CaH_2$) DMF at 0°. Tlc (silica, 90:10 v/v chloroform:methanol) indicated the presence of the NHS ester of DECAS and disappearance of starting material after 1 hr.

To 8.7 mg of polyclonal sheep antidigoxin in 0.5 ml of PBS was added 0.5 ml of pH8.5 sodium pyrophosphate (0.1M). To the vigorously stirred 0° antibody solution was added slowly two 25-μl portions of the NHS ester solution of DECAS prepared above. Each addition took 2-3 minutes and was followed by a 20-30 pulse sonication at 0°.

After 2 hr. the reaction was centrifuged and the supernatnt (1 ml) was chromatographed on an 18-ml bed of Sephadex G-25 prepared in a pH7 buffer consisting of 50 mM sodium phosphate, 0.15M NaCl, and 10 mg/ml of sodium cholate. The void volume band was collected and after 3 days at 4° was centrifuged to remove a small amount of blue precipitate and chromatographed on 18 ml of insoluble potato starch made up in PBS. The fast-moving blue band showed no non-covalent dye when spotted on silica and eluted with acidic dimethoxyethane. After concentration by ultrafiltration to 1.2 ml, UV analysis in PBS/BCD with DECAS and sheep digoxin as standards showed the product to have $\lambda$max at 650 and a dye: protein ratio of 2.2.

EXAMPLE 5

Assay for Digoxin

Buffers:
  PBS
  PBS/BCD
  PBS/10% BGG
  PBS/BGG/Triton
  PBS/SDS
Reagents:
  Sheep antidigoxin-dye conjugate prepared as in Example 4
  Magnetic particle-digoxigenin-aminodextran reagent prepared as in Example 3 diluted with an equal volume of PBS/BGG-Triton (M-Dig)
  Digoxin calibrators in PBS/BGG-Triton at the following concentrations:
    $1.0 \times 10^4$ ng/ml
    $3.16 \times 10^3$ ng/ml
    $1.0 \times 10^3$ ng/ml
    $3.16 \times 10^2$ ng/ml
    $1.0 \times 10^2$ ng/ml
    0 ng/ml
Protocol:
  To 10 μl of PBS/BGG-Triton was added 25 μl of Ab-Dye
    50 μl of calibrator was added.
    A 20 min incubation (capped) followed.
  100 μl of M-Dig was added.
    A 2-hr incubation (vertical rotor) followed.
    Tubes were centrifuged and supernatants decanted.
  200 μl of PBS/BGG-Triton was added with 1-2 pulses of sonication.
    Tubes were centrifuged 1 min and supernatants decanted.
  200 μl of PBS/BGG-Triton was added with 1-2 pulses of sonication.
    Tubes were centrifuged 1 min and supernatants decanted.
  200 μl of PBS/BGG-Triton was added with 1-2 pulses of sonication.
    Tubes were centrifuged 1 min and supernatant decanted.
  50 μl of PBS/SDS was added with 20-30 pulses of sonication.
    Tubes were warmed for 20 sec under hot tap water.
  150 μl of PBS/BCD was added
    Tubes were centrifuged 1 min.
  190 μl of the supernatant was diluted with 750 μl of PBS/BCD
    Solutions were read on a fiber optic laser fluorescence reader ($\lambda$ex=633 nm)
Results are summarized in Table 1.

TABLE 1

| Digoxin (ng/ml) | Fluorescence (units) |
|---|---|
| $1.0 \times 10^4$ | 368 |
| $3.16 \times 10^3$ | 427 |
| $1.0 \times 10^3$ | 488 |
| $3.16 \times 10^2$ | 645 |
| $1 \times 10^2$ | 692 |
| 0 | 708 |

The above results demonstrate that a rapid, accurate, sensitive assay for digoxin can be carried out in accordance with the teaching of the present invention. An increase in concentration of digoxin of two orders of magnitude ($1 \times 10^2$ to $1 \times 10^4$ ng/ml) resulted in a substantial decrease in the observed fluorescence from 692 to 368. Furthermore, the above assay readily distinguished between digoxin concentrations of $1 \times 10^2$ ng/ml and $3.16 \times 10^2$ ng/ml.

EXAMPLE 6

Preparation of 1,3-bis[4-(N-ethyl-carboxymethylamino)-2-hydroxyphenyl]-2,4-dihydroxycyclobutenediylium dihydroxide, (DCAS) and its bis hydrazide To a solution of 161 g of 3-acetamidophenol in 800 ml of tetrahydrofuran was added dropwise over 1-2 hr 275 ml of a 1.0M solution of borane-methyl sulfide in dichloromethane. The reaction was heated to reflux 4-5 hr and then poured slowly into 1 l of methanol. The solvent was evaporated to a heavy syrup which deposited crystals on cooling and scratching. The solid was collected by filtration and redisolved in methanol. Evaporation and crystallization as above gave a 74% yield of 3-(ethylamino) phenol.

Methyl bromoacetate (10.7 g, 70 mmole), 3-(ethylamino) phenol from above (4.8 g, 35 mmole), and ethyl diisopropyl amine (4.45 g, 35 mmole) were combined in 25 ml of toluene. The mixture was heated at 100° C. for 30 min. and then evaporated under vacuum and chromatographed on a silica gel column using 5% (v/v) methanol/methylene chloride. The combined fractions were washed with saturated sodium bicarbonate and neutralized with 0.1N HCL. The combined fractions were dried over $Na_2SO_4$ and evaporated to give 7.24 g of N-ethyl-N-3-hydroxyphenyl glycine methyl ester.

The above product (0.78 g, 3.73 mmole) was combined with squaric acid (0.19 g, 1.67 mmole) in a 10 ml round bottom flask. n-Butyl alcohol (1 ml) and 4 ml of benzene were added and the mixture was refluxed overnight. The solvent was removed by rotary evaporation.

The dried product from above (50 mg) was dissolved in 10 ml of DMF and 1 ml of anhydrous hydrazine was added. The mixture was stirred at room temperature overnight. The reaction mixture was diluted with 50 ml of water and dilute HCl was added to give a precipitate, which was collected and washed with water and dried on a suction filter.

EXAMPLE 7

Preparation of Squarate Dye-Digoxin Conjugate

To a vigorously stirred solution of 390 mg (0.5 mmol) of digoxin dissolved in 5 ml of N,N-dimethylformamide maintained at 0° C. was added dropwise 214 mg (1.0 mmol) of sodium periodate dissolved in 5 ml of deionized water. The reaction was stirred at 0° for four hours; then an additional 107 mg (0.5 mmol) of solid sodium periodate was added. The reaction was allowed to warm gradually to room temperature with stirring for a further 16 hours.

The reaction was diluted with 10 ml of water and stirred for 20 minutes. Then 10 ml of saturated sodium chloride was added and the reaction was extracted with $3 \times 15$ ml of ethyl acetate. The ethyl acetate phases were combined, washed with $6 \times 15$ ml of water, $1 \times 15$ ml of saturated sodium chloride, and dried over sodium sulfate. Filtration of the drying agent and removal of ethyl acetate by rotary evaporation yielded 246 mg (31% yield) of digoxin dialdehyde, which by thin-layer chromatography on silica gel (chloroform—methanol (9:1); Rf 0.43) was greater than 95% pure. The product was used in subsequent reactions without further purification.

To 25 mg (0.05 mmol) of DCAS bis-hydrazide prepared as described in Example 6 and 78 mg (0.10 mmol) of digoxin dialdehyde prepared as above was added 2 ml of dry dimethylformamide and 17 μl (0.10 mmol) of N,N-diisopropylethylamine. The reaction was stirred at room temperature under nitrogen for 48 hours, during which time a new product formed. By thin layer chromatography, using chloroform-methanol (9:1, v/v) as developing solvent; this product had $R_f$ 0.45 and was blue-green in color. The reaction mixture was evaporated to dryness by rotary evaporation and purified by preparative thin layer chromatography on two 20×20 cm silica gel type GF preparative plates, using chloroform-methanol (9:1, v/v) as developing solvent. The band corresponding to the produce at $R_f$ 0.45 was scraped off the plate and eluted from the silica gel with methanol. Evaporation of methanol yielded a dark greenish-blue solid product.

EXAMPLE 8

Preparation of Sheep Anti-Digoxin-Gallocyanine Conjugate

To a stirred solution of 16 mg of sheep anti-digoxin in 10 ml of pH 8.0 phosphate buffered saline at 0° was added dropwise 0.1 ml of a 0.1M solution of gallocyanine NHS ester (prepared by a procedure similar to that of Example 4 for the preparation of the NHS ester of DECAS) in dry DMF over a five minute period. After stirring at 0°-4° for 18 hours, 0.1 ml of 4M hydroxylamine hydrochloride was added all at once and stirring was continued for thirty minutes at 0°-4°. The blue solution was then purified by gel filtration, dialysis, and centrifugation to give 7.6 ml of 1.44 mg/ml blue antibody solution. The solution contained an average of 2.6 moles gallocyanine per mole of anti-digoxin. The absorption maxima of the conjugate were at 278 nm and 625 nm, and the relative quantum yield of the conjugate was determined to be 0.02.

EXAMPLE 9

Competitive Assay

An assay buffer and three reagent stock solutions in the assay buffer were prepared:

Assay Buffer: pH 7.4 10 mM phosphate buffered saline which is 10 mM in β-cyclodextrin and 0.1% in rabbit serum albumin.

Squarate Dye-Digoxin Conjugate: $1.1 \times 10^{-7}$M in squarate dye and $2.2 \times 10^{-7}$M in digoxin.

Digoxin: 1000 ng/ml.

Sheep Anti-digoxin-Gallocyanine Conjugate: 13.4 mg/ml, or $8.4 \times 10^{-5}$M in antibody.

Assay Protocol:

To plastic assay cups was added 10 μl of Squarate Dye-Digoxin Conjugate stock solution, 12 μl of Antibody-Gallocyanine stock solution, digoxin stock solution of volumes 0, 1, 2, 5, 10, 20, 50, 75, and 100 μl, and assay buffer sufficient to bring the total assay volume to 200 μl. The assay solutions were incubated at room temperature for one hour. Then, 800 μl of assay buffer was added and the fluorescence was measured on a fiber optic fluorometer, using a He-Ne laser at 632.8 nm as the excitation source and measuring the emission at 660±10 nm. The results appear in Table 2.

TABLE 2

| Digoxin (ng/ml) | Fluorescence (kHz) |
| --- | --- |
| 0 | 17.96 ± 1.4 |
| 1 | 18.33 ± 0.39 |
| 2 | 19.50 ± 0.27 |
| 5 | 27.48 ± 0.22 |
| 10 | 29.06 ± 0.39 |
| 20 | 31.10 ± 0.31 |
| 50 | 30.70 ± 0.45 |
| 75 | 30.81 ± 0.18 |
| 100 | 30.81 ± 0.15 |

The above results demonstrate that a rapid, accurate, senstive assay for digoxin can be carried out in accordance with the teaching of the present invention. An increase in concentration of digoxin of two orders of magnitude (1 to 100 ng/ml) resulted in asubstantial increase in the observed fluorescence from 18.33 to 31.23 kHz. Furthermore, the above assay readily distinguished between low levels of digoxin concentrations such as, for example, 1 and 2 ng/ml.

EXAMPLE 10

Preparation of 1,3-bis[4-(diethylamino)-2-hydroxy phenyl]-2,4-dihydroxycyclobutenediylium dihydroxide, bis(inner salt) (DEAS)

DEAS was prepared as follows: Squaric acid (741 mg, 65 mmol) was mixed with stirring, with 2.16 g, 13 mmole 3-N,N-diethylaminophenol in 90 ml of n-butanol:toluene (2:1). The mixture was refluxed overnight with azeotropic removal of water. Progress of the reaction was followed by thin layer chromatography (tlc) using methanol:toluene (1:9). Next, the reaction mixture was distilled to remove about 40 ml of toluene, and then the reaction mixture was cooled to room temperature. Crystalline product was separated by filtration and dried at room temperature to give 2.5 g of product. UV (DMF) λmax 650 nm, ε=240,000, fluorescence (DMF) 650/666 nm.

EXAMPLE 11

Assay for the Determination of the D (Rho) Blood Group Antigen

A saturated solution of DEAS in dimethylformamide (DMF) was prepared and then diluted 1:10 (by volume) with DMF. Fifty μl of the diluted DEAS solution was mixed dropwise with 1 ml of an O (Rho) positive whole blood sample under continuous vortexing. Ten μl of this mixture was mixed with 10 μl of antibody (commercially available typing reagent) specific for the D (Rh$_o$) blood group antigen. The mixture was held for one minute at ambient temperature and then diluted with 1.5 ml of phosphate buffer containing serum albumin and sucrose.

The medium was analyzed for a change in fluorescence as a result of agglutination of cells by means of the limited volume method and apparatus for particle counting disclosed in U.S. Ser. No. 397,285, filed July 12, 1982. The single fiber end of a "Y"-shaped fiber optics coupler obtained from Kaptron, Inc., Palo Alto, Calif. (Splitter-Monitor, Model FOMS-850-P), was submerged in the medium. The fiber had a diameter of 50 microns and produced an excitation cone with a half angle of 12° and an effective sampling volume of $1 \times 10^{-7}$ ml. Excitation light from a He-Ne laser (632.9 nm) was fed into one of the two branch fibers. The portion of the fluorescence emitted from the cells which entered the submerged fiber end was split at the fiber juncture to transmit equal halves back along the two branch fibers. The portion traveling through the second branch fiber was then read on a high-gain EMI photomultiplier after filtering out interference within gate times of one millisecond at the rate of one every 0.1 second for periods of time ranging from 50 to 500 seconds. The average number of fluorescent pulses per gate time was then determined by computer.

Two types of control runs were made to establish a standard emission level.
(a) Samples that were typed as D (Rh$_o$) negative by conventional typing were assayed in the same way.
(b) A commercially available "Rh control" reagent which includes all the ingredients of a D (Rh$_o$) typing reagent except for the antibody was used in the above assay in place of the antibody reagent.

The results from samples from five positive and five negative individuals are summarized in Table 1.

TABLE 1

| Type | Signal* |
| --- | --- |
| D (Rh$_o$) positive | 84 |
|  | 108 |
|  | 72 |
|  | 46 |
|  | 74 |
| D (Rh$_o$) negative | 18 |
|  | 23 |
|  | 22 |
|  | 17 |
|  | 20 |
| Control | 21 |
|  | 19 |

TABLE 1-continued

| Type | Signal* |
| --- | --- |
|  | 17 |

*Signal was obtained by fluctuation analysis as described in the specification. Signals greater than 40 were regarded as positive.

EXAMPLE 12

The assay of Example 11 was repeated for blood group antigens A, B, and O using antibody specific for the A(α A) and B(α B) blood group antigens and antibodies obtained from type O individuals (α A,B), respectively. DEAS was complexed with β-cyclodextran following the teaching of Kinsland, supra. The results are summarized in Table 3.

TABLE 3

| Blood Type | Reagent | Signal* |
| --- | --- | --- |
| A | αA | 98 |
|  | αB | 13 |
|  | αA,B | 252 |
|  | Control - no reagent | 11 |
| B | αA | 10 |
|  | αB | 65 |
|  | αA,B | 272 |
|  | Control - no reagent | 16 |
| O | αA | 18 |
|  | αB | 20 |
|  | αA,B | 34 |
|  | Control - no reagent | 13 |

*Signal was obtained by fluctuation analysis as described in the specification. Signals greater than 40 were regarded as positive.

The above date demonstrate that the improved fluorescent assay method of the invention employing a squarate dye as a fluorescent compound and a He-Ne laser as an energy source for excitation of the squarate dye has utility for assaying for a wide variety of analytes such as blood typing antigens. The method is simple and rapid. Generally, the method may be performed in a single step. The effects, on the sensitivity of the assay, of background interference from other components of a sample are minimized. The result of the assay may be obtained without a separation or washing step.

The invention has been described in detail with particular reference to the above embodiments. It will be understood, however, that variations and modifications can be effected within the spirit and scope of the invention.

What is claimed is:

1. A conjugate of a squaraine dye covalently or noncovalently bonded to a member of a specific binding pair, said conjugate being of the formula

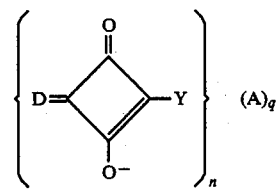

wherein:
D and Y are the same or different and each consists of a chain of from 1 to 6 moieties selected from the group consisting of —CH= and —N=, said chain having alternating single and double bonds and terminating in a double or single bonded atom selected from the group consisting of O, S, and disubstituted nitrogen, wherein the sum of the number of said moieties and said terminal atoms in both D and Y is an even number, said chain, or part thereof including the terminal atom, being aliphatic or part of one or more alicyclic or aromatic rings, or a combination thereof, said chain or rings, or atoms having zero, one, or more substituents consisting of from 1 to 30 atoms other than hydrogen, which atoms are selected from the group consisting of carbon, oxygen, nitrogen, sulfur, halogen, arsenic, silicon, selenium and phosphorus wherein said substituents may be taken together to form one or more rings which may be alicyclic or aromatic, wherein at least one of D or Y is bonded to A;

A is a group consisting of at least one member of a specific binding pair (sbp) consisting of ligand and its complementary receptor;

n is a number from 1 up to the molecular weight of A divided by 100; and q is 1 or 2.

2. The conjugate of claim 1 wherein A is an antigen.

3. The conjugate of claim 1 wherein A is an antibody.

4. The conjugate of claim 1 wherein the sbp member is bound to a polymer.

5. A conjugate of a squaraine dye covalently or non-covalnetly bonded to a member of a specific binding pair, said conjugate being of the formula

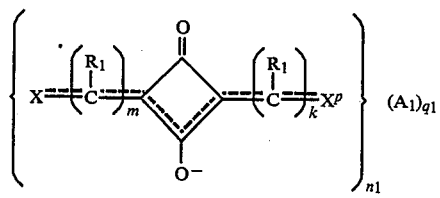

wherein:
m is 1 to 4;
k is 1 to 4;
m+k is an even number;
X is O, S, or N(R$_1$)$_2$;
p is (−) when X is O or S and (+) when X is N(R$_1$)$_2$;
R$_1$ is independently selected from a group consisting of hydrogen and substituents having from 1 to 30 atoms other than hydrogen selected from the group consisting of carbon, oxygen, nitrogen, sulfur, halogen, arsenic, silicon, selenium, and phosphorus, wherein R$_1$ may be taken together with one or more other R$_1$s to form one or more rings, and wherein a hydrogen atom on at least one R$_1$ is replaced by a bond to A$_1$;

n$_1$ is a number from 1 up to the molecular weight of A$_1$ divided by 100;

A$_1$ is a group consisting of at least one member of a specific binding pair (sbp) consisting of ligand and its complementary receptor, wherein A$_1$ is bonded to R$_1$, x, or x$^p$; and q$_1$ is 1 or 2.

6. The conjugate of claim 5 wherein m and k are each 4 and R$_1$ on carbon 1 and R$_1$ on carbon 4 are taken together to form an ethylene group as part of a benzene ring.

7. The conjugate of claim 6 wherein X is N(R$_1$)$_2$.

8. The conjugate of claim 6 wherein X is oxygen.

9. The conjugate of claim 5 wherein m and k are each 2 and X is N(R$_1$)$_2$ and one R$_1$ of N(R$_1$)$_2$ is taken together with R$_1$ on the carbon bearing N(R$_1$)$_2$ to form a five membered ring.

10. The conjugate of claim 9 wherein a benzene ring is fused to the five membered ring.

11. The conjugate of claim 5 wherein A$_1$ is an antigen.

12. The conjugate of claim 5 wherein A$_1$ is an antibody.

13. The conjugate of claim 5 wherein the sbp member is bound to a polymer.

14. A composition of the formula

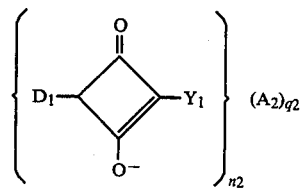

wherein:
q$_2$ is 1 or 2;

A$_2$ is a group consisting of at lest one member of a specific binding pair (sbp) consisting of ligand and its complementary receptor;

n$_2$ is a number from 1 up to the molecular weight of A divided by 100;

D$_1$ is independently selected from the group consisting of

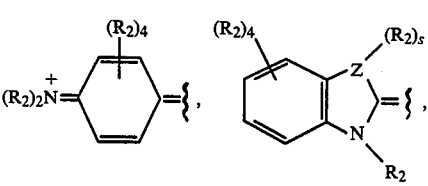

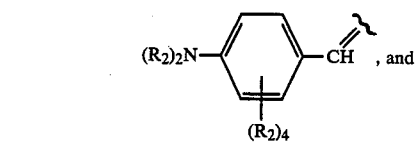

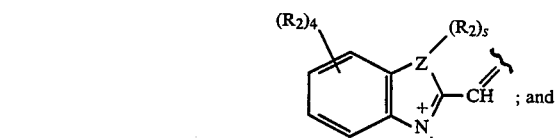

Y$_1$ is independently selected from the group consisting of

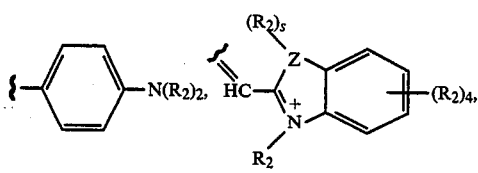

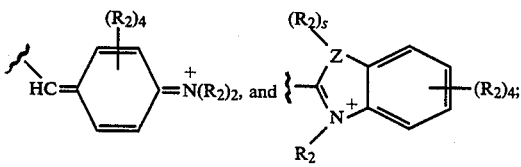

Z in $D_1$ and Z in $Y_1$ are indpendently selected from the group consisting of carbon, nitrogen, oxygen, sulfur, and selenium;

$R_2$ is independently selected from group consisting of hydrogen and substituents having from 1 to 4 atoms other than hydrogen selected from the group consisting of carbon, oxygen, nitrogen, suflur, halogen, arsenic, silicon, selenium, and phosphorus, wherein $R_2$ may be taken together with one or more other $R_2$s to form one or more rings, and wherein a hydrogen atom on at least one $R_2$ is replaced by a bond to $A_2$;

s is 2 when Z is carbon, 1 when Z is nitrogen, and 0 when Z is oxygen, sulfur, or selenium.

15. The conjugate of claim 14 wherein $D_1$ is

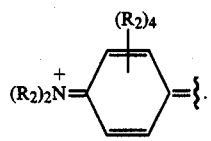

16. The conjugate of claim 14, wherein $R_2$ bound to nitrogen is independently selected from the group consisting of methyl and a group imparting water solubility and $R_2$ bound to carbon is hydrogen, wherein a hydrogen atom of at least one $R_2$ is replaced by a bond or linking group to $A_2$.

17. The conjugate of claim 16 wherein the group imparting water solubility includes a moiety selected from the group consisting of sulfonates and phosphates.

18. The conjugate of claim 14 wherein $D_1$ is

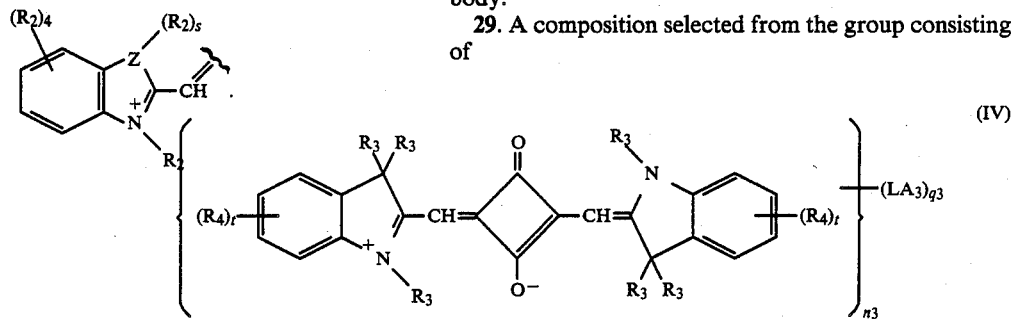

19. The conjugate of claim 18 wherein $Z(R_2)_s$ is isopropylidene.

20. The conjugate of claim 19 wherein up to two of $R_2$ other than $R_2$ bound to Z are groups imparting water solubility and are otherwise hydrogen with the proviso that a hydrogen atom of at least one $R_2$ is replaced by a bond or linking group to $A_2$.

21. The conjugate of claim 14 wherein $Y_1$ is

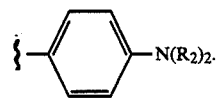

22. The conjugate of claim 21 wherein $R_2$ bound to nitrogen is selected independently from the group consisting of methyl and a linking group to $A_2$.

23. The conjugate of claim 14 wherein $Y_1$ is

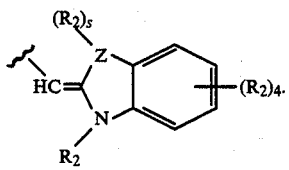

24. The conjugate of claim 23 wherein $Z(R_2)_s$ is isopropylidene.

25. The conjugate of claim 24 wherein up to two of $R_2$ other than $R_2$ bound to Z are groups imparting water solubility and are otherwise hydrogen with the proviso that a hydrogen atom of at least one $R_2$ is replaced by a bond or linking group to $A_2$.

26. The conjugate of claim 14 wherein the sbp member is bound to a polymer.

27. The conjugate of claim 14 wherein $A_2$ is an antigen.

28. The conjugate of claim 14 wherein $A_2$ is an antibody.

29. A composition selected from the group consisting of

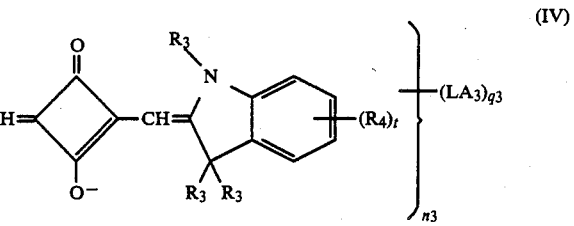

(IV)

and

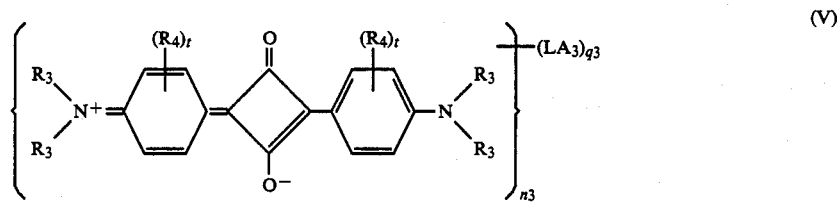

(V)

wherein:

$A_3$ is a member of a specific binding pair;

$n_3$ is a number from 1 up to the molecular weight of $A_3$ divided by 5000;

t is 1 or 2;

$q_3$ is 1 or 2;

$R_3$ is indpendently selected from the group consisting of substituents having 1-10 carbon atoms, 0-6 oxygen atoms, and 0-3 nitroen atoms, and may be taken together to form an alicyclic or aromatic ring;

R4 is indpendently selected from the group consisting of hydroxyl, hydrogen, phosphate, phosphonate, sulfonate, nitro, halogen, amino, and R3; and L replaces any hydrogen of R3 and is a bond or a linking group to A3.

30. The conjugate of claim 29 wherein at least one R3 on nitrogen has a hydrogen replaced by L.

31. The conjugate of claim 30 wherein every remaining R3 on nitrogen is lower alkyl of 1 to 5 carbons.

32. The conjugate of claim 29 wherein t is 1 and R4 is hydroxyl.

33. The conjugate of claim 29 wherein L is selected from the group consisting of non-oxo-carbonyl, carbamoyl, thiocarbamoyl and amino.

34. The conjugate of claim 29 wherein the sbp member is bound to a polymer.

35. The conjugate of claim 29 wherein A3 is an antigen or hapten.

36. The conjugate of claim 29 wherein A3 is digoxin.

37. The conjugate of claim 29 wherein A3 is an antibody.

38. A composition of the formula

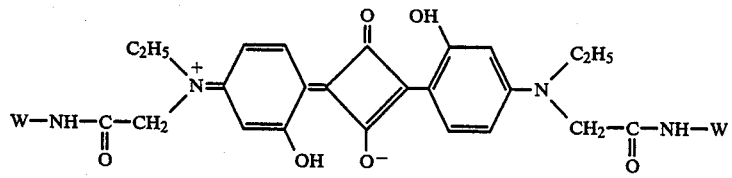

wherein:

W is selected from the group consisting of antibody for digoxin and a digoxin analog capable of binding to anti-digoxin.

39. In a conjugate for use in an assay for determining an analyte in a sample, said compound being a conjugate of a dye and a member of a specific binding pair (sbp) consisting of ligand and its complementary receptor, the improvement which comprises employing a squarate dye as the dye in said conjugate.

40. The conjugate of claim 39 wherein said sbp member is an anitgen or an antibody.

41. The conjugate of claim 39 wherein said sbp member is an antibody.

42. The conjugate of claim 39 wherein said squarate dye has an absorption maximum greater than 600 nm.

43. The conjugate of claim 41 wherein the sbp member is bound to a polymer.

44. In an assay for an analyte in a sample suspected to containing said analyte, which analyte is a member of a specific binding pair (sbp member), said method involving the steps of (1) combining in an assay medium said sample and an sbp member conjugated to a dye and (2) determining the effect of said sample on the fluorescene of said dye, the effect thereof being related to the presence of analyte in said sample, the improvement which comprises employing as said dye a squarate dye.

45. The assay of claim 44 wherein said conjugated sbp member is an antigen or a hapten.

46. The assay of claim 44 wherein said conjuated sbp member is an antibody.

47. The assay of claim 44 wherein said squarate dye has an absorption maximum greater than 600 nm.

48. A method for detecting the presence or amount of analyte in a sample suspected of containing said analyte, wherein said analyte is a member of a specific binding pair consisting of ligand and its complementary receptor, which method comprises combining in an assay medium the sample, the sbp member containing conjugate of claim 1, and a third sbp member, wherein two of the three spb members are complementary to the remaining member, and determining the effect of said sample on the fluorescence of the conjugate of claim 1, the effect thereof being related to the presence or amount of analyte in said sample.

49. The method of claim 48 wherein said third sbp member is conjugated to a compound capable of quenching the fluorescence of the compound of claim 1 when said third sbp member is bound to said conjugate of claim 1.

50. The method of claim 48 wherein said third sbp member is an antibody for the analyte.

51. The method of claim 48 wherein said third sbp member is bound to a particle or to a surface.

52. The method of claim 48 wherein said third sbp member and the sbp member of the conjugate of claim 1 are both antibodies for said analyte.

53. A method for detecting the presence or amount of analyte in a sample suspected of containing said analyte, said analyte being a member of a specific binding pair (sbp) consisting of ligand and its complementary receptor, which method comprises combining in an assay medium the sample, the sbp member containing conjugate of claim 5, and a third sbp member where two of the three spb members are complementary to the remaining sbp member, and determining the effect of said sample on the fluorescence of the conjugate of claim 5, the effect thereof being related to the presence or amount of analyte in said sample.

54. The method fo claim 53 wherein said third sbp member is conjugated to a compound capable of quenching the fluorescence of the compound of claim 7 when said third sbp member is bound to the conjugate of claim 5.

55. The method of claim 53 wherein said third sbp member is an antibody for the analyte.

56. The method of claim 53 wherein said third sbp member is conjugated to a particle or a surface.

57. The method of claim 53 wherein said third sbp member and the sbp member of the conjugate of claim 5 are both antibodies for said analyte.

58. A method for detecting the presence or amount of analyte in a sample suspected of containing said analyte, said analyte being a member of a specific binding pair (sbp) consisting of ligand and its complementary receptor, which method comprises combining in an assay medium the sample, the sbp member containing conjugate of claim 14, and a third sbp member where two of the three sbp members are complementary to the remaining sbp member, and determining the effect of said sample on the fluorescence of the conjugate of claim 14, the effect thereof being related to the presence or amount of analyte in said sample.

59. The method of claim 58 wherein said third sbp member is conjugated to a compound capable of quenching the fluorescence of the compound of claim 14 when said third sbp member is bound to the compound of claim 14.

60. The method of claim 58 wherein said third sbp member is an antibody for the analyte.

61. The method of claim 58 wherein said their sbp member is bound to a particle or a surface.

62. The method of claim 58 wherein said third sbp member and the sbp member of the conjugate of claim 14 are both antibodies for said analyte.

63. A method for detecting the presence or amount of an analyte in a sample suspected of containing said analyte, said analyte being a member of a specific binding pair (sbp) consisting of ligand and its complementary receptor, which method comprises
combining in an assay medium the sample, the sbp member containing conjugate of claim 29, and a third sbp member wherein two of the three sbp members are complementary to the remaining sbp member, and
determining the effect of said sample on the fluorescence of the conjugate of claim 29, the effect thereof being related to the presence or amount of analyte in said sample.

64. The method of claim 63 wherein said third sbp member is conjugated to a compound capable of quenching the fluorescence of the conjugate of claim 29 when said third sbp member is bound to the conjugate of claim 29.

65. The method of claim 63 wherein the said third member is an antibody for the analyte.

66. The method of claim 63 wherein said third sbp member is bound to a particle or a surface.

67. The method of claim 63 wherein said third sbp member and the sbp member of the compound of claim 29 are both antibodies for said analyte.

68. A method for determining digoxin in a sample suspected of containing digoxin, which method comprises
combining in an assay medium the sample, the conjugate of claim 38 wherein W is a digoxin analog, and an antibody for digoxin, and
determining the effect of the sample on the fluorescence of said medium, the effect thereof being related to the presence digoxin in said sample.

69. The method of claim 68 wherein the quencher is gallocyanine conjugated to said antibody.

70. A method for determining digoxin in a sample suspected of containing digoxin, which method comprises
combining in an assay medium the sample, the conjugate of claim 38 wherein W is antibody for digoxin, and a second conjugate comprising a digoxin analog conjugated to particles, and
determining the effect of said sample on the flourescence of said medium or said particles, the effect thereof being related to the presence of digoxin in said sample.

71. In an assay for a material of interest in a sample suspected of containing the material of interest wherein said assay comprises the steps of (1) combining in an assay medium said sample with a fluorescent compound to generate a signal in relation to the presence or amount of the material of interest in said sample and (2) irradiating said fluorescent compound with an energy source for excitation of said fluorescent compound, the improvement which comprises employing a squarate dye as the flourescent compound and a helium/neon laser as the energy source.

72. The assay of claim 71 wherein said squarate dye is water compatible.

73. In a fluorescent assay employing as a reagent a fluorescent compound conjugated to a member of a specific binding pair wherein said pair consists of ligand and its complementary receptor and said assay is for the determination of an analyte which is also a member of a specific binding pair, the binding of said conjugate to said analyte, or a specific binding pair (sbp) member complex of said analyte, being indicative of the presence of said analyte, said assay comprising the steps of
(1) combining a sample suspected of containing said analyte with said reagent and
(2) determining the binding of said reagent to said analyte or an sbp member complex of said analyte, the improvement which comprises employing in said assay a reagent that is a squarate dye conjugated to a member of a specific binding pair.

74. In a method for detecting the presence of a determinant site or a receptor by employing a fluorescent reagent having a fluorescent compound bound to a member of a specific binding pair, wherein the binding of said fluorescent reagent to said determinant site or said receptor, or a specific binding pair (sbp) member complex of said determinant site or said receptor, is determined as indicative of the presence of said determinant site or said receptor, said assay comprising the steps of
(1) combining said determinant site or said receptor with said fluorescent reagent and
(2) determining the extent of binding of said reagent to said determinant site or said receptor, or an sbp member complex of said determinant site or said receptor, the improvement which comprises employing a fluorescent reagent that is a conjugate of a squarate dye and a member of a specific binding pair.

75. The method of claim 74 wherein said determinant site or said receptor is on the surface a cell.

76. A kit for use in determining the presence or amount of an analyte in a sample suspected of containing said analyte, said analyte being a member of a specific binding pair (sbp), said kit comprising in packaged combination
a first compound comprising a squarate dye conjugated to a second sbp member,
a second compound comprising a third sbp member wherein two of the three sbp members are complementary to the remaining sbp member, and
ancillary materials as required.

77. The kit of claim 76 wherein said squarate dye has an absorption maximum greater than 600 nm.

78. The kit of claim 76 wherein said sbp members are selected from the group consisting of antigens or haptens and antibodies.

79. The kit of claim 76 wherein the sbp members in said first compound and in said second compound are both antibodies for said analyte.

80. The kit of claim 76 wherein said second compound is antibody for the analyte.

81. The kit of claim 76 wherein the analyte is digoxin.

82. The kit of claim 76 wherein the sbp member in said first compound is an antibody for a hapten and said second compound comprises a complementary hapten conjugated to a particle.

* * * * *